US008265950B2

(12) United States Patent
Howe et al.

(10) Patent No.: US 8,265,950 B2
(45) Date of Patent: Sep. 11, 2012

(54) SYSTEM FOR PRE-PROCESSING DRUG BENEFIT CLAIMS ACCORDING TO PROCESSED DRUG LISTS

(75) Inventors: Frederick Howe, Rancho Santa Fe, CA (US); Paul M. Momita, San Diego, CA (US)

(73) Assignee: MedImpact Healthcare Systems, Inc., San Diego, CA (US)

( * ) Notice: Subject to any disclaimer, the term of this patent is extended or adjusted under 35 U.S.C. 154(b) by 393 days.

(21) Appl. No.: 12/338,993

(22) Filed: Dec. 18, 2008

(65) Prior Publication Data

US 2010/0161351 A1 Jun. 24, 2010

(51) Int. Cl.
*G06Q 10/00* (2006.01)
*G06Q 50/00* (2006.01)
(52) U.S. Cl. ............................................. 705/2
(58) Field of Classification Search .................... 705/2, 3
See application file for complete search history.

(56) References Cited

U.S. PATENT DOCUMENTS

| | | | |
|---|---|---|---|
| 5,301,105 A | 4/1994 | Cummings, Jr. | |
| 5,704,044 A | 12/1997 | Tarter et al. | |
| 5,737,539 A | 4/1998 | Edelson et al. | |
| 5,845,255 A | 12/1998 | Mayaud | |
| 6,108,635 A | 8/2000 | Herren et al. | |
| 6,195,612 B1 | 2/2001 | Pack-Harris | |
| 6,283,761 B1 | 9/2001 | Joao | |
| 7,165,077 B2 | 1/2007 | Kalies | |
| 7,490,047 B2 | 2/2009 | Brown et al. | |
| 7,505,917 B2 | 3/2009 | Howe et al. | |

(Continued)

FOREIGN PATENT DOCUMENTS

WO WO 95/24010 9/1995

(Continued)

OTHER PUBLICATIONS

MedImpact Medicare Part D 2009 Pre-Processing Drug List (PPDL) White Paper, Updated Mar. 25, 2008. pp. 1-5.

(Continued)

*Primary Examiner* — Luke Gilligan
*Assistant Examiner* — Charles P Coleman
(74) *Attorney, Agent, or Firm* — Knobbe Martens Olson & Bear LLP (57) ABSTRACT

A method of processing drug claims, by: (a) receiving a claim; (b) sorting the claim for processing by determining which processed drug list the claim belongs with; and then (c) processing the claim according to the particular processed drug list to which the claim belongs. A hierarchy of drug lists are used in a preferred order. If the drug is found on the first drug list, the system then moves directly to the processing stage. However, if the drug is not found on the first list, the system checks whether the drug is on the second drug list. If the drug is found on the second drug list, the system then moves directly to the processing stage, etc. Preferably, the drug list hierarchy is as follows: (i) home infusion drug list; (ii) drug only listed as a Medicare Part B drug list; (iii) drug listed as either Medicare Part B or D drug list; (iv) required special class drug list; (v) nebulized drug list; (vi) over the counter drug list; (vii) Medicare statutorily excluded non-Part D drug list; (viii) enhanced benefit system drug list; (ix) Medicare Part D or Medicare Part D covered under an enhanced benefit drug list, and (x) a vaccine drug list.

34 Claims, 2 Drawing Sheets

U.S. PATENT DOCUMENTS

| | | | |
|---|---|---|---|
| 2001/0037216 A1* | 11/2001 | Oscar et al. | 705/2 |
| 2002/0049617 A1 | 4/2002 | Lencki et al. | |
| 2002/0095316 A1 | 7/2002 | Toan et al. | |
| 2002/0111832 A1 | 8/2002 | Judge | |
| 2002/0147617 A1 | 10/2002 | Schoenbaum et al. | |
| 2002/0169727 A1 | 11/2002 | Melnick et al. | |
| 2003/0154106 A1 | 8/2003 | Marks | |
| 2004/0073457 A1 | 4/2004 | Kalies | |
| 2004/0143171 A1 | 7/2004 | Kalies | |
| 2004/0143594 A1 | 7/2004 | Kalies | |
| 2004/0148195 A1 | 7/2004 | Kalies | |
| 2004/0148196 A1 | 7/2004 | Kalies | |
| 2004/0148198 A1 | 7/2004 | Kalies | |
| 2005/0065821 A1 | 3/2005 | Kalies, Jr. | |
| 2005/0071193 A1 | 3/2005 | Kalies | |
| 2006/0129357 A1 | 6/2006 | Francis et al. | |
| 2006/0178915 A1 | 8/2006 | Chao | |
| 2006/0184391 A1 | 8/2006 | Barre et al. | |
| 2006/0271402 A1 | 11/2006 | Rowe et al. | |
| 2007/0050210 A1 | 3/2007 | Wiley, II | |
| 2007/0106623 A1 | 5/2007 | Melnick et al. | |
| 2007/0250341 A1 | 10/2007 | Howe et al. | |
| 2008/0312956 A1 | 12/2008 | Momita et al. | |
| 2009/0177490 A1 | 7/2009 | Howe et al. | |
| 2010/0057489 A1 | 3/2010 | Howe et al. | |
| 2010/0287002 A1 | 11/2010 | Barre et al. | |
| 2011/0029321 A1 | 2/2011 | Rourke et al. | |

FOREIGN PATENT DOCUMENTS

| | | |
|---|---|---|
| WO | WO 97/44752 | 11/1997 |

OTHER PUBLICATIONS

MedImpact Medicare Part D 2008 Pre-Processing Drug List (PPDL) White Paper, Updated Mar. 25, 2008. pp. 1-5.

MedImpact Medicare Part D Pre-Processing Drug List (PPDL) White Paper, Updated Jul. 20, 2006. pp. 1-5.

MedImpact Medicare Part D Drug List White Paper, Oct. 13, 2005. pp. 1-4.

"Cost Sharing Strategies for OHP Medical Services." pp. 1-5. Revised Jul. 5, 2001.

Laing, R.O., et al., "Tuberculosis Drug Issues: Prices, Fixed Dose Combination Products and Second Line Drugs", Journal Tuberculosis Disease, 4(12) S194-S207 (Feb. 2000).

Huskamp, H.A., et al., "The Medicare Prescription Drug Benefit: How Will the Game be Played?" Health Affairs, 19(2) 8-23 (Mar.-Apr. 2000).

Lipton, H.L., et al., "Managing the Pharmacy Benefit in Medicare HMOs: What Do We Really Know?" Health Affairs, 19(2) 42-58 (Mar.-Apr. 2000).

* cited by examiner

SYSTEM FOR PRE-PROCESSING DRUG BENEFIT CLAIMS ACCORDING TO PROCESSED DRUG LISTS

TECHNICAL FIELD

The present invention relates to automated systems for pre-processing drug benefit claims.

BACKGROUND OF THE INVENTION

During the initial stages of Medicare Part D implementation in 2005, the U.S. Centers for Medicare and Medicaid Services (CMS) issued guidelines on which drugs would and would not be reimbursed by CMS under Part D. The Medicare Part D benefit introduced a completely new set of rules related to the processing and reporting of claims based upon various drug types. Unfortunately, although CMS created specific categories of drugs, it did not provide sufficiently specific lists or rules necessary to route and flag claims in an automated production environment. As a result, the need exists for an innovative system that could efficiently sort and automate electronic claims adjudication processing.

SUMMARY OF THE INVENTION

The present invention provides a system for adjudicating drug claims by automatically sorting both Medicare reimbursed and non-Medicare reimbursed drug claims according to processed drug lists.

When claims are submitted into the present system, the claims are first sorted on the basis of which drug list or drug lists the drug in question appears on. In accordance with the present invention, the claims can be sorted into Medicare Part B, Medicare Part D, infusion drug claims, or various other categories/lists of drug claims. After the individual claims are automatically sorted into these various categories, the claims can then be all processed according to that particular claim list category. For example, all Medicare Part B claims can be processed as Medicare Part B claims, and all Medicare Part D claims can be processed as Medicare Part D claims, etc.

In accordance with the present invention, sorting may also be based upon whether a particular drug on the claim in question has been previously placed onto one drug list or another for the particular patient in question. For example, has the drug in question previously been prescribed for use as a Medicare Part B drug for this particular patient? If so, then the determination can automatically be made to continue to process the drug claim the same way for that particular patient (i.e. process it as a Medicare Part B drug claim).

After the claims have been sorted, they are then processed per the standard processing for the particular drug list so identified. For example, if the drug is for an over the counter drug covered under a Medicare Part D administrative fee, the claim is then processed as an over the counter drug claim under Medicare Part D. Similarly, if the drug in the claim in question is for a Medicare Part B drug, the claim is processed as a Medicare Part B drug claim.

In accordance with the present invention, an initial set of processed drug lists may be received by the owner or operator of the present system on a periodic basis. These lists can then be analyzed by the owner or operator of the present system to determine if they need to be changed or updated. As such, these processed drug lists can be updated and modified over time as required. As a result, the construction of the final processed drug lists can be based upon not only information made available from the CMS, but also the expertise of pharmacists at the system operator (and their own development of drug formularies).

For example, a weekly drug list update can be obtained having a list of all National Drug Codes (NDCs). This weekly drug list may have attributes changed and/or any new NDCs that have come onto the market since the last update. For example, changes to the NDC drug list may occur when the FDA recalls a drug or when a manufacturer voluntarily recalls a drug. A pharmacist or pharmacists working with the present system can then ensure that the processed drug lists used by the present system ensure that drugs are placed into the correct lists based on the interpretation of CMS regulatory statutes or guidance. These finalized processed drug lists are then used in the present system.

An advantage of the present invention is that it automatically flags (and sorts) claims for automated processing. Thus, it significantly increases the speed and efficiency of Medicare pharmacy claims processing. In addition, it also increases accuracy and decreases the potential for errors made during pharmacy benefit claims processing. Another advantage of the present system is that its usage of processed drug lists assists with the proper reporting. This greatly simplifies the processing of Medicare Part D benefit drug claims.

In accordance with the present invention, a method is provided for receiving a claim, sorting the claim for processing and then processing the claim. The sorting involves a series of steps in which the claim is compared to various processed drug lists (one after another) until a match to the drug on the claim is found. When a match is found, the claim is then processed according to how claims are normally processed for the claims involving drugs on that particular drug list. As such, a hierarchy of drug lists are used in a preferred order. If the drug is found on the first drug list, the system then moves directly to the processing stage. However, if the drug is not found on the first list, the system checks whether the drug is on the second drug list. If the drug is found on the second drug list, the system then moves directly to the processing stage, etc.

In one preferred aspect, the present invention provides a method of sorting and processing drug claims, comprising:
(a) receiving a claim;
(b) sorting the claim for processing by:
(i) determining if the claim is for a drug listed as a home infusion drug, and if not, then;
(ii) determining if the claim is for a drug that is only listed as a Medicare Part B drug, and if not then;
(iii) determining if the claim is for a drug that is listed as either a Medicare Part B or Medicare Part D drug, and if so, then determining whether the drug has been previously determined to be a Medicare Part B drug or a Medicare Part D drug for the particular patient associated with the claim; and if not then;
(iv) determining if the claim is for a drug that is listed as a required special class drug, and if not, then;
(v) determining if the claim is for a drug that is listed as a nebulized drug, and if not, then;
(vi) determining if the claim is for a drug that is listed as an over the counter drug covered under a Medicare Part D administrative fee, and if not, then;
(vii) determining if the claim is for a drug that is listed as a Medicare statutorily excluded non-Part D drug, and if not, then;
(viii) determining if the claim is for a drug that is listed as always being covered under an enhanced benefit system under Medicare Part D; and if not, then;

(ix) determining whether the claim is for a drug that is listed as eligible for either Medicare Part D or Medicare Part D covered under an enhanced benefit system; and if so, then determining whether the drug has been previously determined to be covered under the enhanced benefit system for the particular patient associated with the claim; and (c) processing the claim as follows:
(i) if the claim is for a drug that is listed as a home infusion drug, then processing the claim as a home infusion drug claim;
(ii) if the claim is for a drug that is only listed as a Medicare Part B drug, then processing the claim as a Medicare Part B drug claim;
(iii) if the claim is for a drug that is listed as a Medicare Part B drug that has previously been determined to be a Medicare Part B drug for the particular patient associated with the claim, then processing the claim as a Medicare Part B drug claim;
(iv) if the claim is for a drug that is listed as a Medicare Part D drug that has previously been determined to be a Medicare Part D drug for the particular patient associated with the claim, then processing the claim as a Medicare Part D drug claim;
(vi) if the claim is for a drug that is listed as eligible for either Medicare Part B or Medicare Part D, and no previous determination has been made as to whether the drug is a Medicare Part B drug or a Medicare Part D drug for the particular patient associated with the claim, then rejecting the claim;
(vii) if the claim is for a drug that is listed as a required special class drug, then processing the claim as a required special class drug claim;
(viii) if the claim is for a drug that is listed as a nebulized drug, then processing the claim as a nebulized drug claim;
(ix) if the claim is for a drug that is listed as an over the counter drug covered under a Medicare Part D administrative fee, then processing the claim as an over the counter drug claim under Medicare Part D;
(x) if the claim is for a drug that is listed as always being covered under an enhanced benefit system under Medicare Part D, then, then processing the claim under an enhanced benefit system under Medicare Part D;
(xi) if the claim is for a drug that is listed as a Medicare Part D drug that is covered under an enhanced benefit system for the particular patient associated with the claim, then processing the claim under an enhanced benefit system under Medicare Part D; and
(xii) if the claim is for a drug that is listed as a Medicare Part D drug that is not covered under an enhanced benefit system for the particular patient associated with the claim, then processing the claim as a standard Medicare Part D drug claim.

An advantage of the present method is that it can account for the scenario whereby certain drugs are found on multiple processed drug lists. Thus, a specific hierarchy of steps is required in order to efficiently and accurately route and filter the claim in accordance with CMS rules and guidelines. For example, drugs belonging to the over the counter drug list covered under the Part D administrative fee almost invariably also belong to the Medicare statutorily excluded non-Part D drug list. CMS rules dictate that over the counter drugs covered under the Part D administrative fee are covered under Part D, overriding their otherwise Medicare statutorily excluded non-Part D drug status. Therefore, using the above hierarchy of first handling the over the counter step drugs at step (ix) prior to step (x) allows for accurate processing of these drugs within the present processing system.

BRIEF DESCRIPTION OF THE DRAWINGS

The attached

DETAILED DESCRIPTION OF THE DRAWINGS

The present invention provides a system for adjudicating drug benefit claims by automatically sorting both Medicare reimbursed and non-Medicare reimbursed drug claims according to processed drug lists. Specifically, the present invention provides an automated method of sorting and processing drug benefit claims, by: (a) receiving a claim; (b) sorting the claim for processing by determining which drug list the claim belongs with; and then (c) processing the claim according to the particular drug list to which the claim belongs.

In accordance with the invention, a hierarchy of processed drug lists are used in a preferred order. If the drug in question is found on the first drug list, the system then moves directly to the processing stage (i.e. for claims on that first drug list). However, if the drug is not found on the first list, the system checks whether the drug is on the second drug list. If the drug is found on the second drug list, the system then moves directly to the processing stage (i.e. for claims on that second drug list), etc. Thus, the sorting involves a series of steps in which the claim is compared to various drug lists (one after another) until a match is found. When a match is found between the drug in the claim and a drug on a drug list, the claim is then processed according to how claims are normally processed for the claims involving drugs on that particular drug list. For example, if the drug is for an over the counter drug covered under a Medicare Part D administrative fee, the claim is then processed according to the way in which the system normally processes over the counter drug claims under Medicare Part D. Similarly, if the drug is for a Medicare Part B drug, the claim is processed according to the way in which the system normally processes Medicare Part B drug claims, etc.

Preferably, the drug list hierarchy is as follows: (i) "home infusion" drug list; (ii) "drug only listed as a Medicare Part B drug" list; (iii) "eligible for either Medicare Part B or D" drug list; (iv) "required special class" drug list; (v) "nebulized drug" list; (vi) "over the counter drug covered under Medicare Part D" drug list; (vii) "Medicare statutorily excluded non-Part D" drug list; (viii) "enhanced benefit system" drug list; and (ix) "eligible for either Medicare Part D or Medicare Part D under an enhanced benefit system" drug list.

For example, if it is determined that the claim is for a drug listed as a "home infusion drug", the claim is immediately processed as a home infusion drug claim. However, if the claim is for a drug not listed as a home infusion drug, then it is determined if the claim is for a "drug that is only listed as a Medicare Part B drug". If the claim is for a drug that is listed as a "drug that is only listed as a Medicare Part B drug", then the claim is immediately processed as a Medicare Part B drug claim, and so on down the hierarchy of decision steps. As can be seen, the drug in the claim in question is compared to each of the drug lists in sequence to see if the drug on the claim belongs to that particular drug list. If the drug in the claim does not match the first drug list, the system queries whether it matches the second drug list. If the drug in the claim does not match the second drug list, the system queries whether it matches a third drug list. And so on. Once a match is found, the claim is then processed.

In accordance with the present invention, the various drug lists may be "processed". What this means is that the owner or operator of the present system and method may take part in creating, managing and updating these various drug lists. These drug lists may preferably be created (i.e. "processed") prior to the arrival of the claim into the system. It is to be understood, however, that the present invention is not so limited, and that the drug lists may instead be created (i.e. "processed") concurrent with, or after the arrival of the claim into the system as well.

In addition, it is to be understood that the present invention is a system for "pre-processing drug benefit claims". In this broader context, the "pre-processing" of the claims is understood to be the "sorting" of the claims according to the various drug lists matching the claims. After this "pre-processing" (i.e.: sorting) is done, the final step is to process the claim. Thus, the present invention provides a novel system of routing, sorting, and filtering claims through the myriad of Part D specific rules occurs prior to the "regular" claims processing steps normally performed via existing PBM systems, such as evaluating formulary status or refill limitations.

For example, a pharmacist or pharmacists working with the present system can ensure that the processed drug lists used in the present system has drugs that are placed into the correct lists based on the interpretation of CMS regulatory statutes or guidance. Currently, there is no definitive statement as to what drugs are to be placed on which drug list, either from CMS or from a nationally recognized drug clearinghouse. As such, pharmacists using the present system may build (i.e.: "process") and then use these sets of drug lists. Maintenance of these processed drugs lists may optionally occur on a weekly basis, consistent with new updates received from a drug data source such as First Data Bank of San Bruno, Calif.

The ongoing maintenance of the processed drug lists may optionally utilize data from any or all of at least the following sources to keep these lists current: (1) CMS Part D Formulary Guidance, (2) CMS Formulary Reference File Updates, (3) the CMS DESI (Drug Efficacy Study Implementation) Website, (4) FDA resources, (5) CMS Coverage Determinations via Prescription Drug Event (PDE) monitoring, and (6) Durable Medical Equipment Regional Carriers (DMERCs). Once the processing of these drug lists is complete, the system may then proceed through the rest of the adjudication to determine formulary and tier status, as well as any other benefit edits and restrictions that would apply.

Figure 1A:
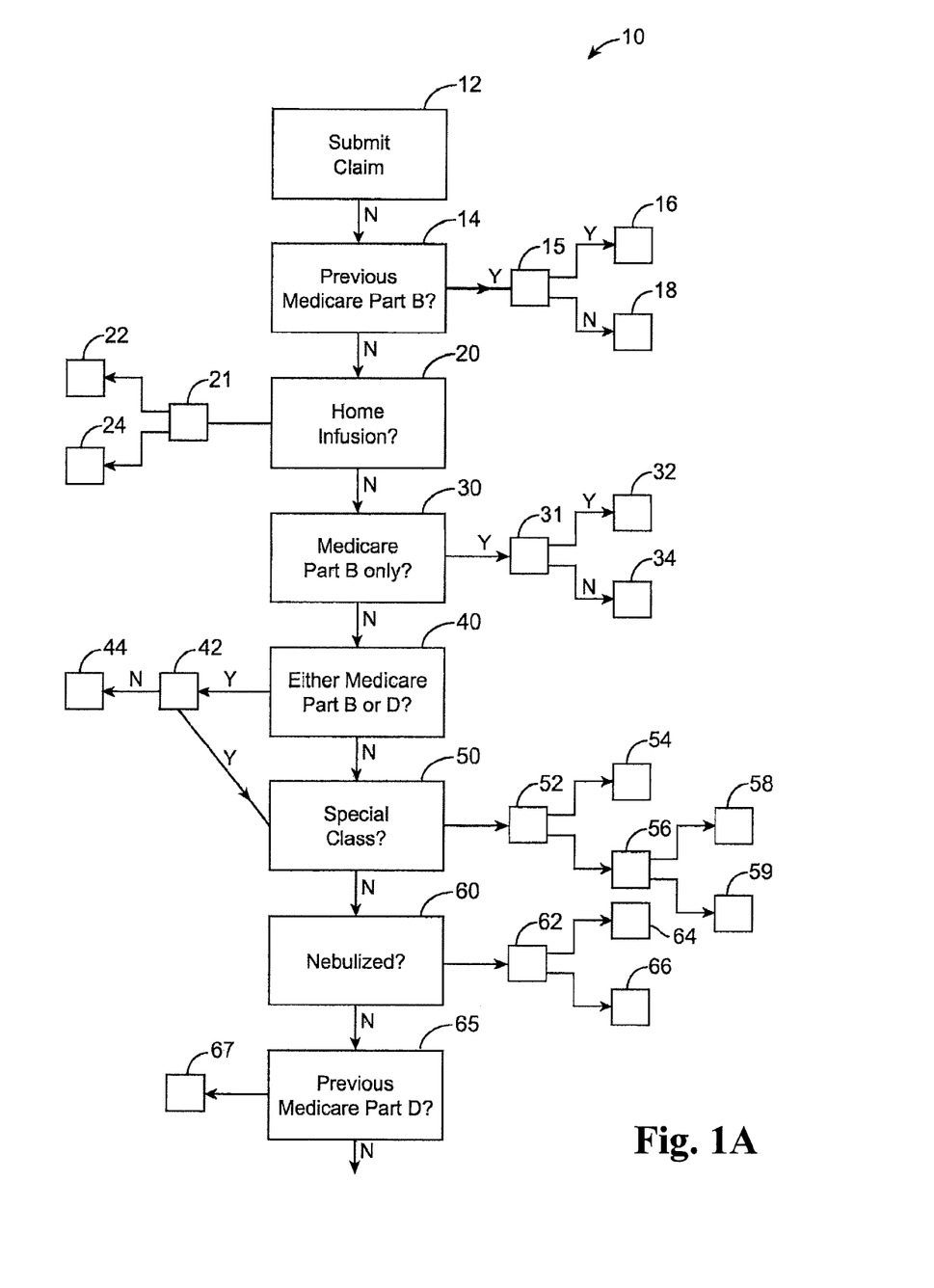
FIG. 1A and FIG. 1B are a flowchart of the preferred method.
Figure 1B:
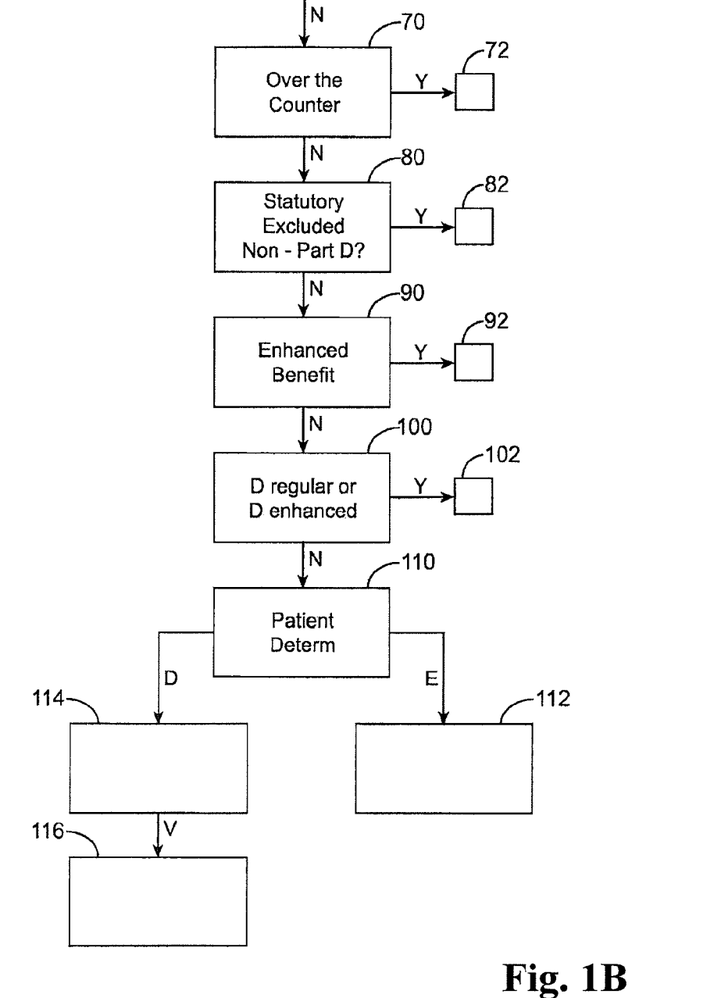

Reference will now be made to the attached FIGURE which is a flowchart illustrating the present method 10 is provided, as follows.

As will be explained in detail below, the present invention provides a method 10 of processing drug claims, comprising: (a) receiving a claim at step 12; and then (b) sorting the claim for processing (steps 14, 20, 30, 40, 50, 60, 65, 70, 80, 90, 100 and 110), and then processing the claim according to which category it has been sorted into (steps 16, 18, 22, 24, 32, 34, 44, 54, 58, 59, 64, 66, 67, 72, 82, 92, 102, 112, 114 and 116).

Claims are sorted as follows. First, at step 14, an optional step of determining whether the claim is for a drug that has been previously determined to be Medicare Part B drug for the particular patient associated with the claim is made.

If the drug on the claim is for a drug previously prescribed or otherwise determined to be a Medicare Part B drug for the particular patient associated with the claim, the system proceeds to step 15 where it is next determined if the client utilizing the present method is also set up to accept processing of such claims. (Note: a number of different clients may simultaneously use the present system. These clients may be corporations with the operator of the present system simultaneously processing drug claims for each of these different clients). As such, the present system is flexible enough so as to accommodate client-specific coverage configurations and parameters for pharmacy claims processing. If the particular client utilizing the present method is indeed set up to accept processing of such claims, then the system proceeds to step 16 and the claim is processed as a "Medicare Part B" drug claim. However, if the particular client serviced by the present method is not set up to accept processing of such claims, the system instead proceeds to step 18 and the claim is rejected.

Next, at step 20, a determination is made whether the drug on the claim matches a drug listed on the "home infusion" processed drug list. If the drug on the claim matches a drug listed on the "home infusion" processed drug list, the system then proceeds to step 21 where it is next determined if the client utilizing the present method is also set up to accept processing of such claims. If the particular client serviced by the present method is indeed set up to accept processing of such claims, then the system proceeds to step 22 and the claim is processed as a "home infusion" drug claim. However, if the client utilizing the present method is not set up to accept processing of such claims, the system instead proceeds to step 24 and the claim is rejected. The drug list used at step 20 preferably represents Medicare Part D home infusion drugs that are available as part of a bundled service under Medicare Part C. Examples of these drugs include various drugs that are administered by an external infusion pump.

Next (after the claim has passed through steps 14 and 20 without matching either drug list), the claim then proceeds to step 30. At step 30, a determination is made whether the drug for the claim in question is for a drug that is only listed as a Medicare Part B drug. If the drug on the claim matches a drug listed on the "Medicare Part B only" processed drug list, the system proceeds to step 31 where it is next determined if the client utilizing the present method is also set up to accept processing of such claims. If the client utilizing the present method is indeed set up to accept processing of such claims, then the system proceeds to step 32 and the claim is processed as a "Medicare Part B only" drug claim. However, if the client utilizing the present method is not set up to accept processing of such claims, the system instead proceeds to step 34 and the claim is rejected. The drug list used at step 30 of "Medicare Part B only" drugs represents drugs that CMS has indicated should always only be covered under Medicare Part B. Examples of these drugs include certain oral cancer drugs and hemophilia factor drugs.

Next (assuming the claim has passed through steps 14, 20 and 30), the claims proceeds to step 40. At step 40, a determination is made whether the drug for the claim in question is for a drug that is listed as eligible for either Medicare Part B or Medicare Part D. If the drug on the claim is a drug listed as eligible for either Medicare Part B or Medicare Part D on the processed drug list, the system proceeds to step 42 where it is next determined whether the drug has been previously been prescribed or otherwise determined to be a Medicare Part B drug or to be a Medicare Part D drug for the particular patient associated with the claim. If no such previous determination has been made, the system proceeds to step 44, and the claim is denied due to the fact that a determination is required before the system can determine whether to process the claim as a Medicare Part B or as a Medicare Part D claim. This determination is preferably managed through a pharmacy benefit process known as "prior authorization". Conversely, if a determination has already been made as to whether the drug should be processed as a Medicare Part B or as a Medicare Part D claim for the particular patient, or if the drug in the claim does not match the "eligible for either Medicare Part B or Medicare Part D" processed drug list, the system instead proceeds directly to step 50.

In optional aspects of the present invention, the drug list used at step 40 represents agents which may be funded through either Medicare Part B or through Medicare Part D depending upon the circumstance or indication. Examples of these drugs include oral antiemetics and Total Parenteral Nutrition (TPN).

In preferred optional aspects of the present invention, the drug list used at step 40 is formulary-specific, and may comprise any suitable representative drug code or codes. For example, the drug list at step 40 may be defined at the representative proxy level, meaning that clients of the system (or the system operator) may define a list of representative proxy NDCs, which can then be expanded into corresponding detailed NDCs in the creation of the particular processed drug lists. Thus, an otherwise uniform drug list can be transformed into one that is formulary-specific based on representative proxy NDC formulary specifications. CMS is moving from a proxy NDC based formulary to a RxNorm based formulary in 2010. In accordance with the present system, formulary coding may also be handled in a more generic manner than by proxy NDC. For example, the system may utilize Proxy NDC, RxNorm, or other representative drug codes to define the drug lists.

At step 50, (assuming the claim has passed through steps 14, 20, 30, 40 and 42) a determination is made whether the drug for the claim in question is for drug listed as a "required special class" drug. If the drug on the claim is a "required special class" drug, then the system proceeds to step 52 at which a determination is made as to whether this drug has previously been prescribed, or is currently prescribed, for this particular patient under their current benefit plan. Thus, processing of the claim as a required special class drug claim comprises determining if the particular patient has previously received the drug If the drug was previously prescribed for this patient (for example, during the past 60 days) under the current benefit plan, the system proceeds to step 54, and the claim is processed. In contrast, if the system does not find previous prescription history of the drug, it then proceeds to check if the member is eligible for transitional benefits (by nature of recently transitioning to a new benefit plan). If the patient is eligible for transition, the system proceeds to step 58 and the claim is processed. Conversely, if the patient is not eligible for transition, the system proceeds to step 59 and the claim is rejected. If the drug is not listed as a "required special class" drug at step 50, the system then proceeds to step 60. The drug list used at step 50 of "special class" drugs currently represents six classes of drugs that CMS has identified as special classes. Different rules apply to these drugs than to other drugs. This drug list includes antidepressants, anticonvulsants, antineoplastics, antipsychotics, immunosuppressants, and HIV agents. Examples of these drugs include Fluoxetine™ and Zidovudine™. These "required special class" drugs represent certain classes of drugs where CMS has indicated that "interruption of therapy in these categories could cause significant negative outcomes to beneficiaries in a short timeframe." This processed drug list is used to identify drugs within these categories and used in conjunction with the automated transition process to allow for continual access or "grandfathering" to medications within this list for the duration of treatment course.

Next, at step 60, (assuming the claim has passed through steps 14, 20, 30, 40, 42 and 50) a determination is made whether the drug for the claim in question is for a drug listed as a "nebulized drug". If the drug on the claim is a drug listed on the "nebulized drug" processed drug list, the system proceeds to step 62, and a determination whether the patient is resident in a long term facility is made. If the patient is resident in a long term facility, the system proceeds to step 64, and the claim is processed as a "nebulized drug" claim. If the patient is instead not resident in a long term facility, the system proceeds to step 66, and the claim is processed as a Medicare Part B drug claim. Alternatively, if the claim in question at step 60 is not for drug listed as a "nebulized drug", the system proceeds to step 65. It is to be understood that the occurance of step 65 is conditional, and sometimes applies and sometimes does not based on member and claim specific factors.

At step 65, a determination is made whether the claim is for a drug that was drug previously determined as a Medicare Part D drug for the particular patient associated with the claim. Optional step 65 thus serves to efficiently bypass the checking of remaining downstream processed drug lists if the determination of a Medicare Part D drug has already been made through a prior authorization process. If the claim is identified as being for a drug previously listed as a Medicare Part D drug for the particular patient associated with the claim, the system proceeds directly to step 67 and the claim is processed as a Medicare Part D claim. If not, the system proceeds directly to step 70.

At step 70, (assuming the claim has passed through steps 14, 20, 30, 40, 42, 50, 60 and 65) a determination is made whether the drug for the claim in question is for an "over the counter" drug covered under the Part D administrative fee. If it is, the system proceeds to step 72 and the claim is processed as an "over the counter" drug claim under a Medicare Part D administrative fee. If not, the system proceeds to step 80. The drug list used at step 70 is preferably client-specific and represents explicit over the counter agents that a Medicare Part D sponsor has received special approval for coverage funded by the administrative fee (as opposed to all available over the counter products). These agents currently cannot require a co-payment to the member. An example of such a drug is Prilosec OTC™.

At step 80, (assuming the claim has passed through steps 14, 20, 30, 40, 42, 50, 60, 65 and 70) a determination is made whether the drug for the claim in question is for a "Medicare statutorily excluded non-Part D" drug. If it is, the system proceeds to step 82 and the claim is processed as a "Medicare statutorily excluded non-Part D drug" drug claim. If not, the system proceeds to step 90. The drug list used at step 80 includes drugs that are "statutory excluded, non-Part D Medicare" medications and devices. Examples include medical devices and most "over the counter" drugs. This drug list represents agents which should not generally be included as a Medicare Part D benefit, either in Medicare Part D regular, or by enhanced coverage.

At step 90, (assuming the claim has passed through steps 14, 20, 30, 40, 42, 50, 60, 65, 70 and 80) a determination is made whether the drug for the claim in question is for a "Medicare Part D drug that is always covered under an enhanced benefit system" drug. If it is, the system proceeds to step 92 and the claim is processed as an "enhanced benefit system" drug claim under Medicare Part D. If not, the system proceeds to step 100. The drug list used at step 90 represents statutory excluded agents which CMS has indicated should only be covered under Medicare Part D via an optional enhanced or supplemental benefit design. These agents cannot be covered under the standard Medicare Part D benefit. Current examples of these drugs include benzodiazepines and barbiturates.

At step 100, (assuming the claim has passed through steps 14, 20, 30, 40, 42, 50, 60, 65, 70, 80 and 90) a determination is made whether the claim is for a drug that is listed as eligible for either "Medicare Part D or Medicare Part D under an enhanced benefit system" processed drug list. If it is not, the system proceeds to step 110. At step 110, a determination is made as to whether the drug in question has been previously determined to be covered under an enhanced benefit system under Medicare Part D for the particular patient in question. If it is, the system then proceeds to step 112 and the claim is processed under an enhanced benefit system under Medicare Part D. Alternatively, a determination can instead be made that the drug in question has been previously determined to be covered under Medicare Part D regular for the particular patient in question. If this is the case, the system instead proceeds from step 110 to 114 where the claim is processed under Medicare Part D regular. Note: If no previous determination was made at step 110, the system may instead default automatically to step 114 (i.e.: the system may assume that the claim is not intended to be covered under an enhanced benefit system).

The drug list used at step 100 represents statutory excluded agents which may be funded through either Medicare Part D or through an enhanced or supplemental benefit design depending upon the circumstance or indication. Examples of these drugs include conditional agents, such as agents for cough or colds.

In an optional feature of step 114, the drug in question may be identified as a being on a "vaccine" drug list. In such a case, the system may proceed directly to step 116 and the claim will then be processed as a "vaccine" drug claim. This is due to CMS Guidance in 2008 that provided direction to Medicare Part D Plan sponsors to process Medicare Part D vaccines with a vaccine administration fee covered and payable to physicians and pharmacies under the Medicare Part D drug benefit. Examples of these drugs include pre-exposure and preventative vaccines. In other optional aspects of the present invention, vaccine claims can be processed as part D claims at prior steps in the process. For example, id the drug in question is a Part D vaccine, the claim may instead be processed as a vaccine claim at any one of steps 54, 64, 67 or 102.

As can be seen, an advantage of the present method is that claims are processed such that as soon as the claim is identified as corresponding to a particular drug list, the claim is then processed in a consistent manner for that drug list. For example, all claims for "over the counter" drugs covered under a Medicare Part D administrative fee are identified and then processed as "over the counter" drug claims under Medicare Part D. All claims for "Medicare Part B" drugs are identified and then processed as "Medicare Part B" drug claims, etc.

As can also be seen, the present invention also comprises determining if a client will accept processing of the claim prior to approving payment for the claim (e.g.: steps 15, 21 and 31). This is particularly advantageous since several clients may be served simultaneously by the same method. One client may accept processing of a particular type of drug claim while another client may not. Steps 15, 21 and 31 all involve determining whether individual clients are set up to accept processing of a particular type of drug claim. Additionally, content of some drug lists including steps 20, 40, and 70 are client-specific based on the particular benefit design strategy.

The processed drug lists (to which the drug in the individual claims are compared) may be constructed on the basis of lists provided by CMS, and/or on the basis of lists devised by an entity operating or otherwise controlling the present method. Alternatively, the construction of the processed drug lists can be contracted out (by the owner/operator of the present method) to other entities' pharmacy and formulary staff, as desired. These persons or entities can periodically update the processed drug lists.

In accordance with the present invention, individual patient determinations as to whether a drug has previously been processed as: (1) a Medicare Part B drug or a Medicare Part D drug; or (2) a Medicare Part D drug or a Medicare Part D drug covered under an enhanced benefit system can be made in steps 42 and 110, respectively. Thus, an advantage of the present invention is that determining which drug list a drug is placed on comprises determining both the identity of the drug, and the drug's method of treatment.

The present invention also provides a computerized system embodying the present method.

In further optional aspects of the invention, a method is provided for processing drug claims wherein it is first determined whether the claim is for a home infusion drug, and thereafter a formulary-specific proxy or suitable representative drug code approach is used to determine whether the drug has been previously determined to be a Medicare Part B drug or a Medicare Part D drug for the particular patient in question. In this aspect of the invention, the claim may be processed by determining if the claim is for a drug that is listed as one or more of the following: (i) a required special class drug; (ii) a nebulized drug; (iii) an over the counter drug covered under a Medicare Part D administrative fee, (iv) a Medicare statutorily excluded non-Part D drug; (v) a Medicare Part D drug that is always covered under an enhanced benefit system; or (vi) a drug that is listed as eligible for either Medicare Part D or Medicare Part D under an enhanced benefit system.

Thus, the present invention also provides a method of sorting and processing drug claims, comprising:
(a) receiving a claim;
(b) sorting the claim for processing by:
(i) determining if the claim is for a home infusion drug, and if not then;
(ii) determining if the claim is for a drug that is listed as either a Medicare Part B or a Medicare Part D drug, and if so, then determining by a formulary-specific proxy or suitable representative drug code approach whether the drug has been previously determined to be a Medicare Part B drug or a Medicare Part D drug for the particular patient associated with the claim; and
(c) processing the claim as follows:
(i) if the claim is for a drug that is listed as a home infusion drug, then processing the claim as a home infusion drug claim;
(ii) if the claim is for a drug that is listed as a Medicare Part B drug that has previously been determined to be a Medicare Part B drug for the particular patient associated with the claim, then processing the claim as a Medicare Part B drug claim;
(iii) if the claim is for a drug that is listed as a Medicare Part D drug that has previously been determined to be a Medicare Part D drug for the particular patient associated with the claim, then processing the claim as a Medicare Part D drug claim; and
(iv) if the claim is for a drug that is listed as eligible for either Medicare Part B or Medicare Part D, and no previous determination has been made as to whether the drug is a Medicare Part B drug or a Medicare Part D drug for the particular patient associated with the claim, then rejecting the claim.

What is claimed is:

1. A non-transitory computer-readable medium comprising instructions that when executed on at least one computer, cause the at least one computer to perform a method of sorting and processing drug claims, the method comprising:
   (a) receiving a claim using the at least one computer;
   (b) sorting the claim for processing by:
      (i) determining if the claim is for a drug listed as a home infusion drug, and if not, then;
      (ii) determining if the claim is for a drug that is only listed as a Medicare Part B drug, and if not then;
      (iii) determining if the claim is for a drug that is listed as either a Medicare Part B or a Medicare Part D drug, and if so, then determining whether the drug has been previously determined to be a Medicare Part B drug or a Medicare Part D drug for the particular patient associated with the claim; and if not then;
      (iv) determining if the claim is for a drug that is listed as a required special class drug, and if not, then;
      (v) determining if the claim is for a drug that is listed as a nebulized drug, and if not, then;
      (vi) determining if the claim is for a drug that is listed as an over the counter drug covered under a Medicare Part D administrative fee, and if not, then;
      (vii) determining if the claim is for a drug that is listed as a Medicare statutorily excluded non-Part D drug, and if not, then;
      (viii) determining if the claim is for a drug that is listed as always being covered under an enhanced benefit system under Medicare Part D, and if not, then;
      (ix) determining whether the claim is for a drug that is listed as eligible for either Medicare Part D or Medicare Part D covered under an enhanced benefit system; and if so, then determining whether the drug has been previously determined to be covered under the enhanced benefit system for the particular patient associated with the claim; and
   (c) processing the claim as follows:
      (i) if the claim is for a drug that is listed as a home infusion drug, then processing the claim as a home infusion drug claim;
      (ii) if the claim is for a drug that is only listed as a Medicare Part B drug, then processing the claim as a Medicare Part B drug claim;
      (iii) if the claim is for a drug that is listed as a Medicare Part B drug that has previously been determined to be a Medicare Part B drug for the particular patient associated with the claim, then processing the claim as a Medicare Part B drug claim;
      (iv) if the claim is for a drug that is listed as a Medicare Part D drug that has previously been determined to be a Medicare Part D drug for the particular patient associated with the claim, then processing the claim as a Medicare Part D drug claim;
      (vi) if the claim is for a drug that is listed as eligible for either Medicare Part B or Medicare Part D, and no previous determination has been made as to whether the drug is a Medicare Part B drug or a Medicare Part D drug for the particular patient associated with the claim, then rejecting the claim;
      (vii) if the claim is for a drug that is listed as a required special class drug, then processing the claim as a required special class drug claim;
      (viii) if the claim is for a drug that is listed as a nebulized drug, then processing the claim as a nebulized drug claim;
      (ix) if the claim is for a drug that is listed as an over the counter drug covered under a Medicare Part D administrative fee, then processing the claim as an over the counter drug claim under Medicare Part D;
      (x) if the claim is for a drug that is listed as always being covered under an enhanced benefit system under Medicare Part D, then, then processing the claim under an enhanced benefit system under Medicare Part D;
      (xi) if the claim is for a drug that is listed as a Medicare Part D drug that is covered under an enhanced benefit system for the particular patient associated with the claim, then processing the claim under an enhanced benefit system under Medicare Part D; and
      (xii) if the claim is for a drug that is listed as a Medicare Part D drug that is not covered under an enhanced benefit system for the particular patient associated with the claim, then processing the claim as a standard Medicare Part D drug claim.

2. The non-transitory computer-readable medium of claim 1, wherein the method further comprises:
   sorting the claim for processing by determining if the claim is for a drug previously determined to be a Medicare Part B drug for the particular patient associated with the claim prior to determining if the claim is for a drug listed as a home infusion drug.

3. The non-transitory computer-readable medium of claim 1, wherein the method further comprises:
   sorting the claim for processing by determining whether the drug has been previously determined to be a Medicare Part B drug or a Medicare Part D drug for the particular patient associated with the claim after determining if the claim is for a drug that is listed as a nebulized drug.

4. The non-transitory computer-readable medium of claim 1, wherein the method further comprises:
   sorting the claim for processing by determining if the claim is for a drug that is listed as a vaccine, and if so, then;
   processing the claim as a vaccine drug claim.

5. The non-transitory computer-readable medium of claim 1, wherein processing the claim further comprises determining if a client will accept processing of the claim prior to approving payment for the claim.

6. The non-transitory computer-readable medium of claim 1, wherein the method further comprises:
   placing drugs onto the drug lists on the basis of lists provided by CMS.

7. The non-transitory computer-readable medium of claim 1, wherein the method further comprises:
   placing drugs onto the drug lists on the basis of lists devised by an operator of the system embodying the method of claim 1.

8. The non-transitory computer-readable medium claim 7, wherein the lists devised by the operator are constructed on the basis of formularies devised by the operator.

9. The non-transitory computer-readable medium claim 7, wherein the lists devised by the operator are constructed on the basis of representative drug codes.

10. The non-transitory computer-readable medium of claim 1, wherein the method further comprises:
    periodically updating the drug lists.

11. The non-transitory computer-readable medium of claim 1, wherein determining whether the drug has been previously determined to be a Medicare Part B drug or a Medicare Part D drug for the particular patient associated with the claim comprises determining if a prior prescription authorization has been made for the particular patient associated with the claim.

12. The non-transitory computer-readable medium of claim 1, wherein determining whether the drug has been previously determined to be a Medicare Part D drug or a Medicare Part D drug covered under an enhanced benefit system for the particular patient associated with the claim comprises determining if a prior prescription authorization has been made for the particular patient associated with the claim.

13. The non-transitory computer-readable medium of claim 1, wherein processing the claim as a required special class drug claim comprises determining if the particular patient has previously received the drug.

14. The non-transitory computer-readable medium of claim 1, wherein processing the claim as a required special class drug claim comprises determining whether the particular patient is in transition between different prescription plans.

15. The non-transitory computer-readable medium of claim 1, wherein processing the claim as a nebulized drug claim comprises determining whether the particular patient is in a long term care facility.

16. The non-transitory computer-readable medium of claim 1, wherein determining which drug list a drug is placed on comprises determining both the identity of the drug, and the drug's method of treatment.

17. The non-transitory computer-readable medium of claim 1, wherein updating the drug lists comprises using data from at least one of CMS Part D Formulary Guidance, CMS Formulary Reference File Updates, CMS DESI (Drug Efficacy Study Implementation) Website, FDA resources, CMS Coverage Determinations via Prescription Drug Event (PDE) monitoring, and Durable Medical Equipment Regional Carriers.

18. The non-transitory computer-readable medium of claim 1, wherein the step of determining if the claim is for a drug that is listed as either a Medicare Part B or a Medicare Part D drug comprises using a formulary or representative drug code approach.

19. The non-transitory computer-readable medium of claim 18, wherein proxies or other representative drug codes used in the formulary approach are devised by an operator.

20. The non-transitory computer-readable medium of claim 18, wherein proxies or other representative drug codes used in the formulary approach are devised by a client of an operator.

21. A computerized system for sorting and processing drug claims, comprising:
 (a) a computer for receiving a claim;
 (b) a system for sorting the claim for processing by:
  (i) determining if the claim is for a drug listed as a home infusion drug, and if not, then;
  (ii) determining if the claim is for a drug that is only listed as a Medicare Part B drug, and if not then;
  (iii) determining if the claim is for a drug that is listed as either a Medicare Part B or a Medicare Part D drug, and if so, then determining whether the drug has been previously determined to be a Medicare Part B drug or a Medicare Part D drug for the particular patient associated with the claim; and if not then,
  (iv) determining if the claim is for a drug that is listed as a required special class drug, and if not, then;
  (v) determining if the claim is for a drug that is listed as a nebulized drug, and if not, then;
  (vi) determining if the claim is for a drug that is listed as an over the counter drug covered under a Medicare Part D administrative fee, and if not, then;
  (vii) determining if the claim is for a drug that is listed as a Medicare statutorily excluded non-Part D drug, and if not, then;
  (viii) determining if the claim is for a drug that is listed as always being covered under an enhanced benefit system under Medicare Part D, and if not, then;
  (ix) determining whether the claim is for a drug that is listed as eligible for either Medicare Part D or Medicare Part D covered under an enhanced benefit system; and if so, then determining whether the drug has been previously determined to be covered under an enhanced benefit system for the particular patient associated with the claim; and
 (c) a system for processing the claim as follows:
  (i) if the claim is for a drug that is listed as a home infusion drug, then processing the claim as a home infusion drug claim;
  (ii) if the claim is for a drug that is only listed as a Medicare Part B drug, then processing the claim as a Medicare Part B drug claim;
  (iii) if the claim is for a drug that is listed as a Medicare Part B drug that has previously been determined to be a Medicare Part B drug for the particular patient associated with the claim, then processing the claim as a Medicare Part B drug claim;
  (iv) if the claim is for a drug that is listed as a Medicare Part D drug that has previously been determined to be a Medicare Part D drug for the particular patient associated with the claim, then processing the claim as a Medicare Part D drug claim;
  (vi) if the claim is for a drug that is listed as eligible for either Medicare Part B or Medicare Part D, and no previous determination has been made as to whether the drug is a Medicare Part B drug or a Medicare Part D drug for the particular patient associated with the claim, then rejecting the claim;
  (vii) if the claim is for a drug that is listed as a required special class drug, then processing the claim as a required special class drug claim;
  (viii) if the claim is for a drug that is listed as a nebulized drug, then processing the claim as a nebulized drug claim;
  (ix) if the claim is for a drug that is listed as an over the counter drug covered under a Medicare Part D administrative fee, then processing the claim as an over the counter drug claim under Medicare Part D;
  (x) if the claim is for a drug that is listed as always being covered under an enhanced benefit system under Medicare Part D, then, then processing the claim under an enhanced benefit system under Medicare Part D;
  (xi) if the claim is for a drug that is listed as a Medicare Part D drug that is covered under an enhanced benefit system for the particular patient associated with the claim, then processing the claim under an enhanced benefit system under Medicare Part D; and
  (xii) if the claim is for a drug that is listed as a Medicare Part D drug that is not covered under an enhanced benefit system for the particular patient associated with the claim, then processing the claim as a standard Medicare Part D drug claim.

22. A non-transitory computer-readable medium comprising instructions that when executed on at least one computer, cause the at least one computer to perform a method of sorting and processing drug claims, the method comprising:

(a) receiving a claim using a computer;

(b) sorting the claim for processing by:
- (i) determining if the claim is for a home infusion drug, and if not then;
- (ii) determining if the claim is for a drug that is listed as either a Medicare Part B or a Medicare Part D drug, and if so, then determining by a formulary or representative drug code approach whether the drug has been previously determined to be a Medicare Part B drug or a Medicare Part D drug for the particular patient associated with the claim; and (c) processing the claim as follows:
- (i) if the claim is for a drug that is listed as a home infusion drug, then processing the claim as a home infusion drug claim;
- (ii) if the claim is for a drug that is listed as a Medicare Part B drug that has previously been determined to be a Medicare Part B drug for the particular patient associated with the claim, then processing the claim as a Medicare Part B drug claim;
- (iii) if the claim is for a drug that is listed as a Medicare Part D drug that has previously been determined to be a Medicare Part D drug for the particular patient associated with the claim, then processing the claim as a Medicare Part D drug claim, and
- (iv) if the claim is for a drug that is listed as eligible for either Medicare Part B or Medicare Part D, and no previous determination has been made as to whether the drug is a Medicare Part B drug or a Medicare Part D drug for the particular patient associated with the claim, then rejecting the claim.

23. The non-transitory computer-readable medium of claim 22, wherein proxies or other representative drug codes used in the formulary approach are devised by an operator.

24. The non-transitory computer-readable medium of claim 22, wherein proxies or other representative drug codes used in the formulary approach are devised by a client of an operator.

25. The non-transitory computer-readable medium of claim 22, wherein the method further comprises:

(d) sorting the claim for processing by determining if the claim is for a drug that is listed as one or more of the following:
- (i) a required special class drug; or
- (ii) a nebulized drug; or
- (iii) an over the counter drug covered under a Medicare Part D administrative fee; or
- (iv) a Medicare statutorily excluded non-Part D drug; or
- (v) a Medicare Part D drug that is always covered under an enhanced benefit system; or
- (vi) a drug that is listed as eligible for either Medicare Part D or Medicare Part D under an enhanced benefit system, and if so, then determining whether the drug has been previously determined to be a regular Medicare Part D drug or a Medicare Part D drug covered under an enhanced benefit system for the particular patient associated with the claim; and (e) processing the claim as follows:
- (i) if the claim is for a drug that is listed as a required special class drug, then processing the claim as a required special class drug claim;
- (ii) if the claim is for a drug that is listed as a nebulized drug, then processing the claim as a nebulized drug claim;
- (iii) if the claim is for a drug that is listed as an over the counter drug covered under a Medicare Part D administrative fee, then processing the claim as an over the counter drug claim under Medicare Part D;
- (iv) if the claim is for a Medicare statutorily excluded non-Part D drug, then processing the claim as a Medicare statutorily excluded non-Part D drug claim;
- (v) if the claim is for a drug that is listed as always being covered under an enhanced benefit system under Medicare Part D, then, then processing the claim under an enhanced benefit system under Medicare Part D;
- (vi) if the claim is for a drug that is listed as a Medicare Part D drug that is covered under an enhanced benefit system for the particular patient associated with the claim, then processing the claim under an enhanced benefit system under Medicare Part D; and
- (vii) if the claim is for a drug that is listed as a Medicare Part D drug that is not covered under an enhanced benefit system for the particular patient associated with the claim, then processing the claim as a standard Medicare Part D drug claim.

26. The non-transitory computer-readable medium of claim 22, wherein processing the claim further comprises determining if a client will accept processing of the claim prior to approving payment for the claim.

27. The non-transitory computer-readable medium of claim 22, wherein the method further comprises:
placing drugs onto the drug lists on the basis of lists provided by CMS.

28. The non-transitory computer-readable medium of claim 22, wherein the method further comprises:
placing drugs onto the drug lists on the basis of lists devised by an operator of the system embodying the method of claim 22.

29. The non-transitory computer-readable medium of claim 22, wherein determining whether the drug has been previously determined to be a Medicare Part B drug or a Medicare Part D drug for the particular patient associated with the claim comprises determining if a prior prescription authorization has been made for the particular patient associated with the claim.

30. The non-transitory computer-readable medium of claim 22, wherein processing the claim as a required special class drug claim comprises determining if the particular patient has previously received the drug.

31. The non-transitory computer-readable medium of claim 22, wherein processing the claim as a required special class drug claim comprises determining whether the particular patient is in transition between different prescription plans.

32. The non-transitory computer-readable medium of claim 22, wherein processing the claim as a nebulized drug claim comprises determining whether the particular patient is in a long term care facility.

33. The non-transitory computer-readable medium of claim 22, wherein determining which drug list a drug is placed on comprises determining both the identity of the drug, and the drug's method of treatment.

34. A computerized system for sorting and processing drug claims, comprising:

(a) a computer for receiving a claim;

(b) a system for sorting the claim for processing by:
- (i) determining if the claim is for a home infusion drug, and if not then;
- (ii) determining if the claim is for a drug that is listed as either a Medicare Part B or a Medicare Part D drug, and if so, then determining by a formulary-specific representative drug code approach whether the drug has been previously determined to be a Medicare Part B drug or a Medicare Part D drug for the particular patient associated with the claim; and (c) a system for processing the claim as follows:
   (i) if the claim is for a drug that is listed as a home infusion drug, then processing the claim as a home infusion drug claim;
   (ii) if the claim is for a drug that is listed as a Medicare Part B drug that has previously been determined to be a Medicare Part B drug for the particular patient associated with the claim, then processing the claim as a Medicare Part B drug claim;
   (iii) if the claim is for a drug that is listed as a Medicare Part D drug that has previously been determined to be a Medicare Part D drug for the particular patient associated with the claim, then processing the claim as a Medicare Part D drug claim; and
   (iv) if the claim is for a drug that is listed as eligible for either Medicare Part B or Medicare Part D, and no previous determination has been made as to whether the drug is a Medicare Part B drug or a Medicare Part D drug for the particular patient associated with the claim, then rejecting the claim.

* * * * *